(12) United States Patent
Tonomura et al.

(10) Patent No.: US 8,282,575 B2
(45) Date of Patent: Oct. 9, 2012

(54) ENDOSCOPIC PUNCTURE NEEDLE AND METHOD OF ACQUIRING TISSUE FROM A TARGET REGION BY USING THE ENDOSCOPIC PUNCTURE NEEDLE

(75) Inventors: Masatoshi Tonomura, Koganei (JP); Teruhisa Seki, Chofu (JP)

(73) Assignee: Olympus Medical Systems Corp. (JP)

( * ) Notice: Subject to any disclaimer, the term of this patent is extended or adjusted under 35 U.S.C. 154(b) by 475 days.

(21) Appl. No.: 12/013,570

(22) Filed: Jan. 14, 2008

(65) Prior Publication Data

US 2008/0139960 A1     Jun. 12, 2008

Related U.S. Application Data

(63) Continuation of application No. PCT/JP2006/313857, filed on Jul. 12, 2006.

(30) Foreign Application Priority Data

Jul. 15, 2005   (JP) .................................. 2005-207232

(51) Int. Cl.
   *A61B 10/00*          (2006.01)
(52) U.S. Cl. ......... 600/566; 600/564; 600/565; 600/567
(58) Field of Classification Search .................. 600/562, 600/563, 564, 565, 566, 567, 568
   See application file for complete search history.

(56) References Cited

U.S. PATENT DOCUMENTS 4,799,494 A    1/1989  Wang
5,601,588 A *  2/1997  Tonomura et al. ............ 606/185
6,514,215 B1 * 2/2003  Ouchi ........................... 600/564
2005/0090763 A1* 4/2005 Wang ............................ 600/564

FOREIGN PATENT DOCUMENTS

| JP | 49-15436    | 4/1974  |
| JP | 62-503007   | 12/1987 |
| JP | 8-150145    | 6/1996  |
| JP | 10-137248   | 5/1998  |
| JP | 2000-070273 | 3/2000  |

(Continued)

OTHER PUBLICATIONS

International Search Report dated Aug. 8, 2006 issued in corresponding PCT Application No. PCT/JP2006/313857.
Written Opinion dated Aug. 8, 2006 issued in corresponding PCT Application No. PCT/JP2006/313857.

(Continued)

*Primary Examiner* — Max Hindenburg
*Assistant Examiner* — Adam Eiseman
(74) *Attorney, Agent, or Firm* — Ostrolenk Faber LLP (57) ABSTRACT

An endoscopic puncture needle includes a sheath, an outer needle, an outer needle moving member, an inner needle, an inner needle moving member, and an operation portion. The outer needle moves along an axial direction of the sheath in the sheath, and is retractable with respect to a distal end of the sheath. The outer needle moving member is arranged at a proximal end portion of the outer needle, and moves the outer needle with respect to the sheath. The inner needle moves in the outer needle along the axial direction of the sheath, and is retractable with respect to a distal end of the outer needle. The inner needle moving member is arranged at a proximal end portion of the inner needle, and moves the inner needle with respect to the outer needle. The operation portion operates the outer needle moving member and the inner needle moving member.

11 Claims, 8 Drawing Sheets

FOREIGN PATENT DOCUMENTS

| | | |
|---|---|---|
| JP | 2000-232983 | 8/2000 |
| JP | 2001-70307 | 3/2001 |
| JP | 2001-112762 | 4/2001 |
| JP | 2001-120556 | 5/2001 |
| JP | 2001-120557 | 5/2001 |
| JP | 2001-149374 | 6/2001 |
| JP | 2001-161699 | 6/2001 |
| JP | 2005-137454 | 6/2005 |
| WO | WO 2004/086977 | 10/2004 |

OTHER PUBLICATIONS

International Preliminary Report on Patentability in corresponding PCT Appln. No. PCT/JP2006/313857 dated Jan. 24, 2008.
Office Action issued by the Japanese Patent Office on Mar. 15, 2010 in connection with corresponding Japanese Patent Application No. 2005-207232 and English language translation.
Japanese Office Action mailed Jul. 6, 2010 in connection with corresponding Japanese Application No. 2005-207232.
English translation of Japanese Office Action dated Jul. 6, 2010.

* cited by examiner

FIG. 7

ENDOSCOPIC PUNCTURE NEEDLE AND METHOD OF ACQUIRING TISSUE FROM A TARGET REGION BY USING THE ENDOSCOPIC PUNCTURE NEEDLE

CROSS REFERENCE TO RELATED APPLICATIONS

This is a Continuation application of PCT Application No. PCT/JP2006/313857, filed Jul. 12, 2006, which was published under PCT Article 21(2) in Japanese.

This application is based upon and claims the benefit of priority from prior Japanese Patent Application No. 2005-207232, filed Jul. 15, 2005, the entire contents of which are incorporated herein by reference.

BACKGROUND OF THE INVENTION

1. Field of the Invention

The present invention relates to an endoscopic puncture needle which is inserted into a surgical instrument insertion channel of an endoscope to be used, and a method of acquiring tissue from a target region by using the endoscopic puncture needle.

2. Description of the Related Art

A biopsy puncture needle having a hollow needle member which is used to acquire tissue from a lung of a patient is disclosed in, e.g., a specification of U.S. Pat. No. 4,799,494. The biopsy puncture needle includes a hollow inner needle which is movable along the axial direction of a hollow outer needle. Therefore, the inner needle is made to protrude with respect to the outer needle at a position where it faces tissue, and the tissue is drawn into the inner needle by suction. At this time, a pressure at a distal end of the needle member is monitored by using a balloon.

BRIEF SUMMARY OF THE INVENTION

One aspect of an endoscopic puncture needle according to the present invention includes: a sheath having flexibility; a hollow outer needle which is movable along an axial direction of the sheath in the sheath and retractable with respect to a distal end of the sheath; an outer needle moving mechanism which is arranged at a proximal end portion of the outer needle and moves the outer needle with respect to the sheath; an inner needle which moves along the axial direction of the sheath in the outer needle and is retractable with respect to the distal end of the outer needle; an inner needle moving mechanism which is arranged at a proximal end portion of the inner needle and moves the inner needle with respect to the outer needle; and an operation portion which is arranged at a proximal end portion of the sheath and operates the outer needle moving mechanism and the inner needle moving mechanism.

One aspect of a method of acquiring tissue from a target region by using an endoscopic puncture needle comprises: arranging the distal end of the sheath on a front side of a target region in a state in which the inner needle and the outer needle are retracted with respect to the distal end of the sheath; operating the outer needle moving mechanism to position the outer needle with respect to the distal end of the sheath; operating the inner needle moving mechanism to make the inner needle protrude from the distal end of the outer needle and puncture tissue in the target region with the inner needle; puncturing the tissue in the target region with the outer needle; operating the inner needle moving mechanism to retract the inner needle with respect to the outer needle; drawing the tissue in the target region into an inner space of the outer needle through the outer needle by suction; operating the outer needle moving means to retract the distal ends of the outer needle and the inner needle with respect to the distal end of the sheath, and pulling out the outer needle from the tissue in the target region.

DETAILED DESCRIPTION OF THE INVENTION

The best mode for carrying out the present invention will now be explained hereinafter with reference to FIGS. 1A to 7.

Figure 1A:
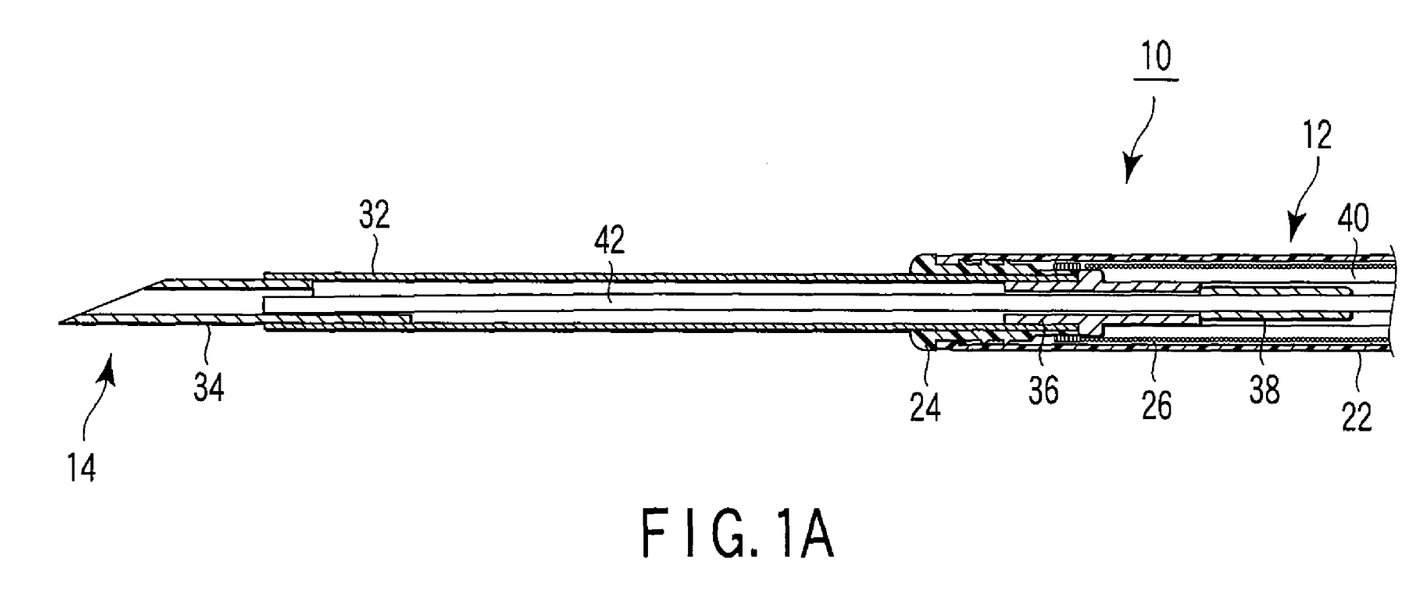
FIG. 1A is a schematic vertical sectional view showing a distal end portion of an endoscopic puncture needle according to an embodiment of the present invention.
Figure 1B:
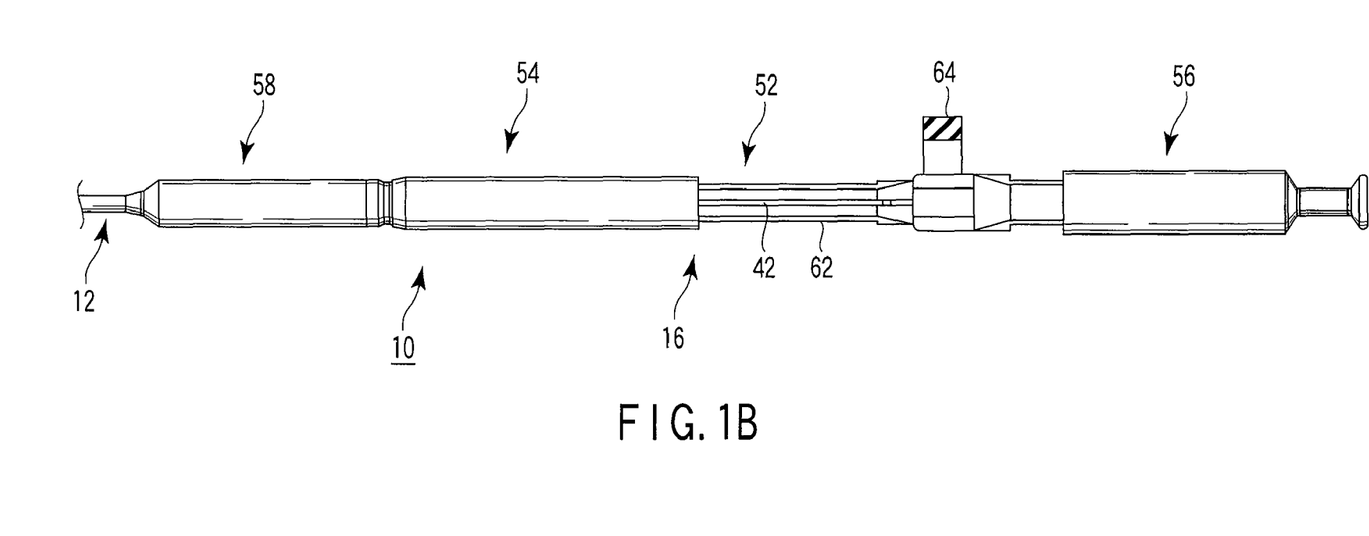
FIG. 1B is a schematic partial cross-sectional view showing a proximal end portion (an operation portion) of the endoscopic puncture needle.

FIG. 1A shows a distal end portion of an endoscopic puncture needle 10, and FIG. 1B shows a proximal end portion (a later-explained operation portion 16) of the same. As shown in FIGS. 1A and 1B, the endoscopic puncture needle 10 according to an embodiment includes a flexible elongated sheath 12, a tubular needle member 14 which is movable in an inner space of the sheath 12, and an operation portion 16 which is provided at a proximal end portion of the sheath and used to move the needle member 14 with respect to the sheath 12. The sheath 12 is formed to be sufficiently longer than an insertion portion of an endoscope or a surgical instrument insertion channel formed to be inserted in the insertion portion in order to be inserted into the surgical instrument insertion channel of the non-illustrated endoscope. Therefore, the needle member 14 is also formed to be sufficiently longer than the insertion portion of the endoscope. In particular, since the needle member 14 must be operated in a state in which it protrudes from a distal end of the sheath 12, it is formed to be further longer than the sheath 12.

Figure 2:
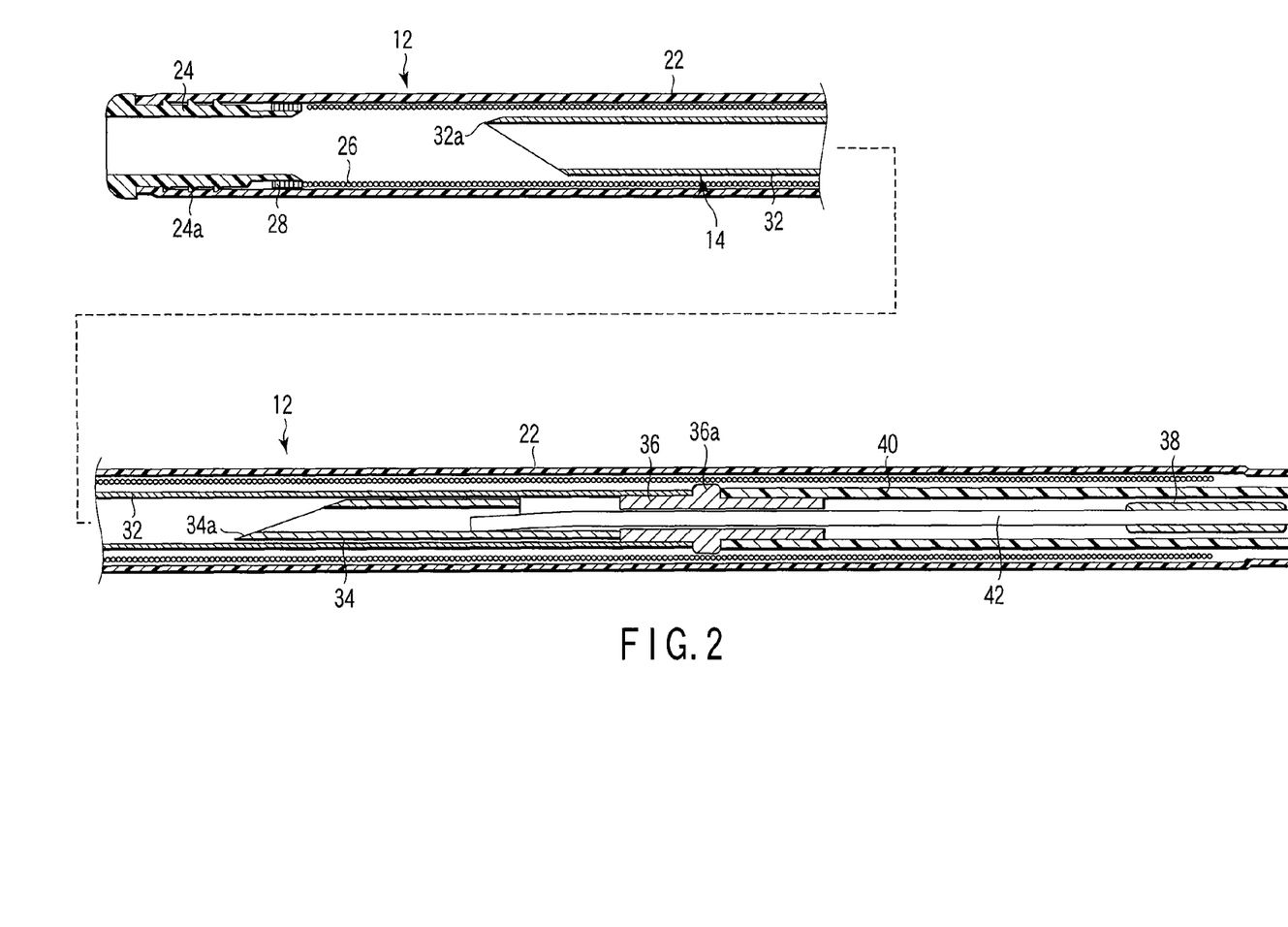
FIG. 2 is a schematic vertical sectional view showing the distal end portion of the endoscopic puncture needle according to the embodiment.

FIG. 2 shows a distal end portion of the sheath 12 and a distal end portion of the needle member 14 as well as a region connected with the distal end portion of the needle member 14. As shown in FIG. 2, the sheath 12 includes a flexible sheath main body 22, a stopper 24 which is arranged at a distal end of the sheath main body 22 and has a substantially annular shape with an inner space and, e.g., hardness, and a protection member 26 which protects the distal end portion of the needle member 14.

The distal end portion of the sheath main body 22 is disposed to the stopper 24 which restricts movement of the needle member 14 toward the distal end portion side of the sheath main body 22. The stopper 24 covers the distal end and an inner peripheral surface of the sheath main body 22 with the distal end portion of the sheath main body 22. The stopper 24 is fixed on the inner peripheral surface of the distal end portion of the sheath main body 22 by protrusions 24a formed on an outer peripheral surface thereof.

The coil-like protection member 26 that protects the needle member 14 is arranged at a proximal end portion of the stopper 24. The protection member 26 is disposed on the inner peripheral surface of the sheath main body 22. The distal end portion of the protection member 26 is held by a holding portion 28 at the proximal end portion of the stopper 24 which holds the protection member 26 when fitted between the sheath main body 22 and the stopper 24.

The needle member 14 includes an outer needle 32, an inner needle 34, an outer needle locking member (a control mechanism) 36, an inner needle locking member (a restriction mechanism) 38, an outer needle moving member 40, and an inner needle moving member 42.

Each of the outer needle 32 and the inner needle 34 is formed of, e.g., a stainless steel material into a hollow structure, and its distal end is sharply formed. That is, opening portions 32a and 34a are respectively formed at the distal ends of the outer needle 32 and the inner needle 34.

The outer needle locking member 36 is arranged at a proximal end portion of the outer needle 32. A distal end portion of the outer needle moving member 40 is arranged on the outer needle locking member 36. Each of the outer needle locking member 36 and the outer needle moving member 40 is formed into a cylindrical (tubular) shape. The outer needle locking member 36 is formed of, e.g., a stainless steel material or a hard plastic material. The outer needle moving member 40 is formed of, e.g., a plastic material such as a fluoroplastic. Therefore, the outer needle moving member 40 has appropriate rigidity to enable movement of the outer needle locking member 36 and the outer needle 32 and also has flexibility enabling deformation in accordance with a deformed state of the surgical instrument insertion channel of the endoscope. The proximal end portion of the outer needle moving member 40 further extends to the proximal end portion side from the proximal end portion of the sheath 12 and is connected with the operation portion 16 (see FIG. 3A).

A flange portion 36a outwardly protruding in a radial direction is formed on an outer peripheral surface of the outer needle locking member 36. The flange portion 36a is locked on an inner peripheral surface of the stopper 24. Movement of the outer needle 32 is restricted when the flange portion 36a of the outer needle locking member 36 comes into contact with the stopper 24. Incidentally, in regard to an internal diameter of each of the outer needle locking member 36 and the outer needle moving member 40, it is preferable that a small gap is present between each of these members and an outer peripheral surface of the later-explained inner needle moving member 42 to some extent.

A distal end portion of the inner needle moving member 42 is fixed at the proximal end portion of the inner needle 34. The inner needle moving member 42 is formed of, e.g., a single wire made of a metal material or a pipe made of a resin material, has flexibility like the outer needle moving member 40. Further, the inner needle moving member 42 is formed with the higher rigidity than that of the outer needle moving member 40. Therefore, a tensile force when a target region is punctured with both the inner needle 34 and the outer needle 32 can be assured, and the flexibility which enables insertion into the surgical instrument insertion channel of the endoscope can be also assured.

The proximal end portion of the inner needle moving member 42 extends to the proximal end portion side of the sheath 12 to be connected with the operation portion 16. The inner needle locking member 38 is arranged at the distal end portion of the inner needle moving member 42. The inner needle locking member 38 is arranged on the outer peripheral surface of the inner needle moving member 42. Moreover, the inner needle locking member 38 is arranged on the proximal end portion side apart from the outer needle locking member 36. Therefore, movement of the inner needle 34 toward the distal end side of the sheath 12 is restricted when the inner needle locking member 38 comes into contact with the proximal end portion of the outer needle locking member 36.

As shown in FIG. 1B, the operation portion 16 includes an operation portion main body 52, first and second slide members 54 and 56 which can slide with respect to the operation portion main body 52, and a connection tube 58 fixed to the first slide member 54.

The operation portion main body 52 includes a cylindrical portion 62, and a luer mouth ring 64 which is formed in a direction perpendicular to the cylindrical portion 62 and to which a syringe (not shown) is attached.

Figure 3A:
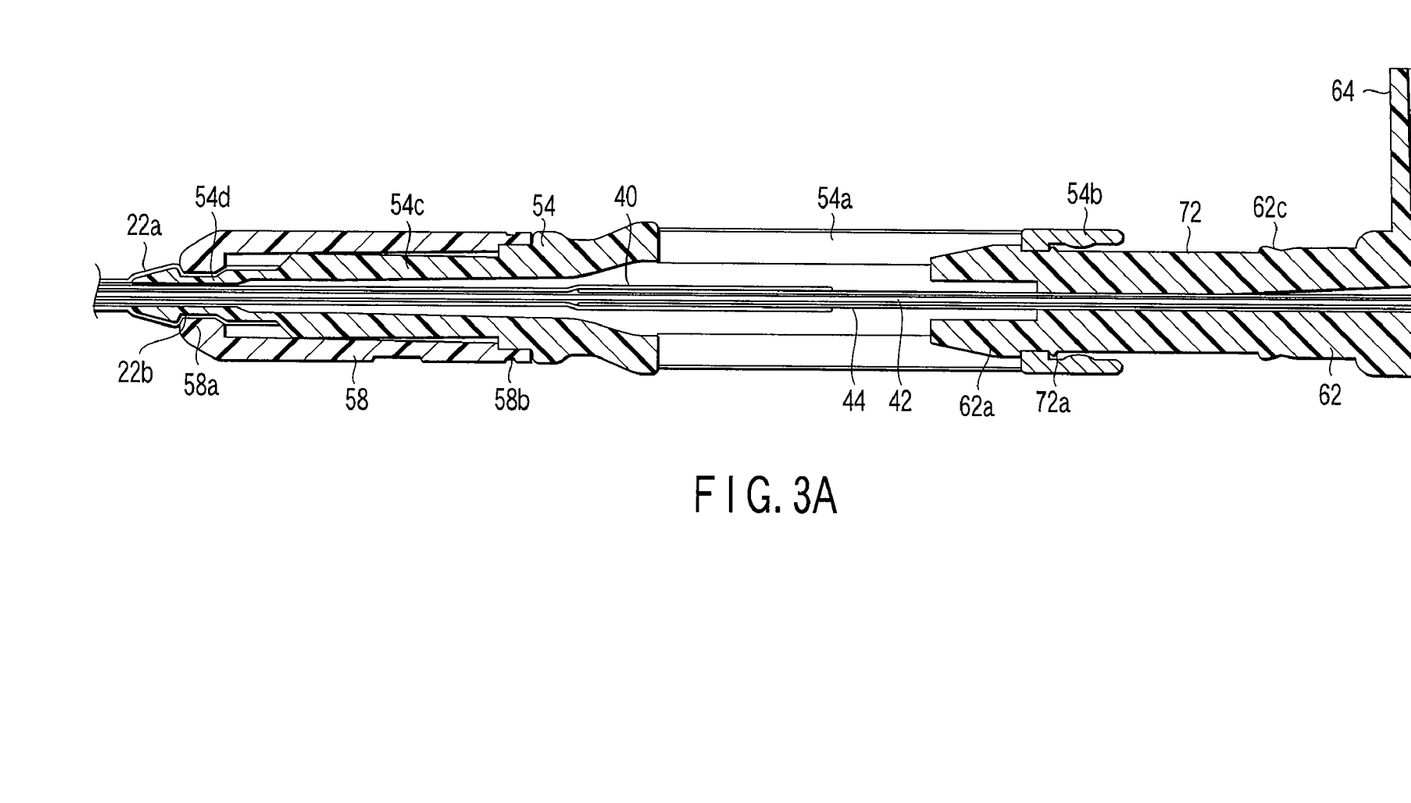
FIG. 3A is a schematic vertical sectional view showing a proximal end portion of a sheath and the operation portion in the endoscopic puncture needle according to the embodiment, especially a distal end portion side apart from a central axis of a luer mouth ring of the operation portion.
Figure 3B:
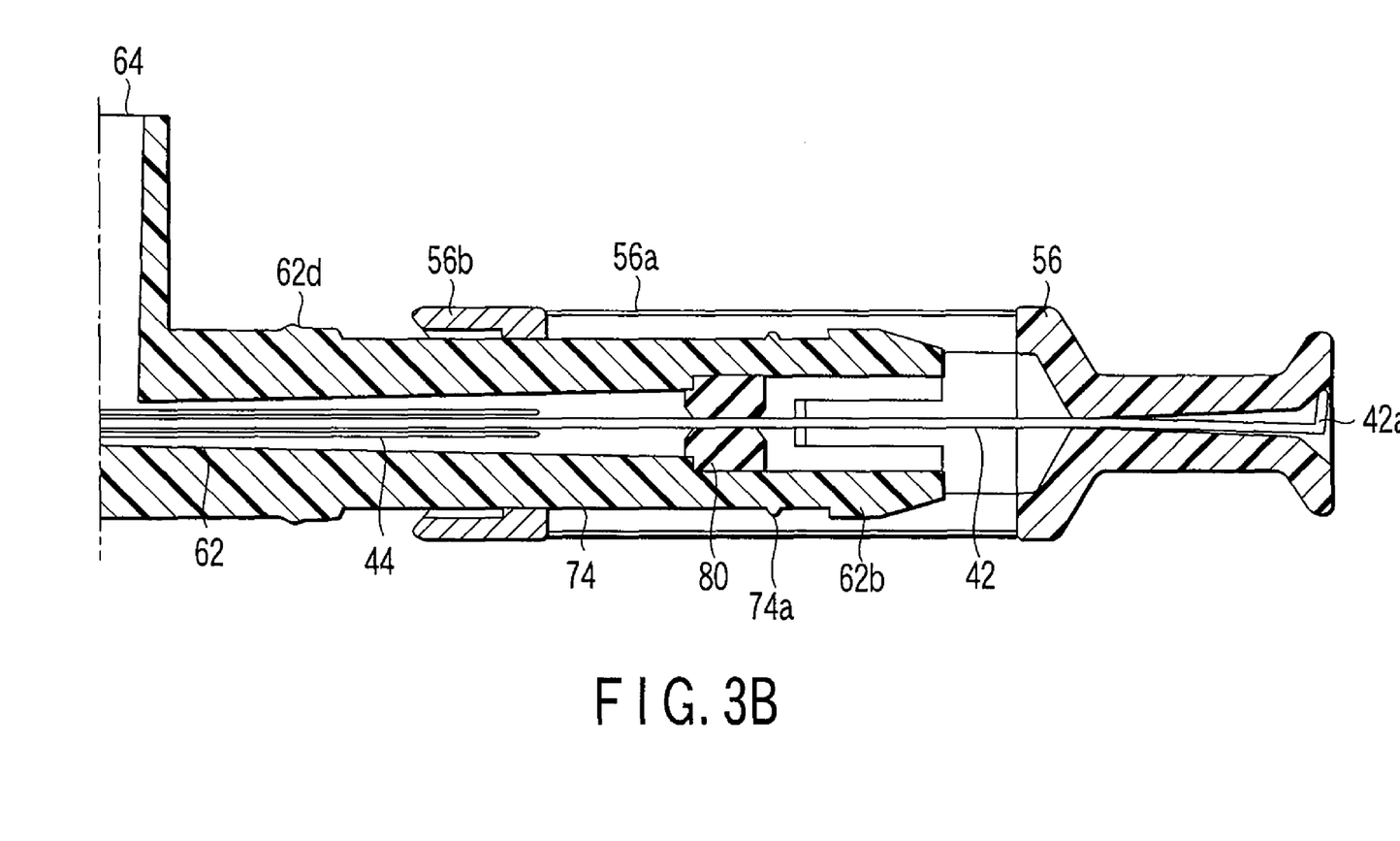
FIG. 3B is a schematic vertical sectional view showing a proximal end portion side apart from the central axis of the luer mouth ring of the operation portion in the endoscopic puncture needle according to the embodiment.

Here, FIG. 3A shows a distal end portion side from a central axis of the luer mouth ring 64 of the operation portion 16, and FIG. 3B shows a proximal end portion side from the central axis of the luer mouth ring 64.

As shown in FIGS. 3A and 3B, an inner space along the central axis of the cylindrical portion 62 communicates with an inner space along a central axis of the luer mouth ring 64. As shown in FIG. 3A, a first slide accepting portion 72 which accepts the first slide member 54 to allow its movement in a predetermined range is formed on an outer peripheral surface of the cylindrical portion 62 on the distal end side. An outwardly protruding convex portion 72a is formed on the distal end portion side of the first slide accepting portion 72. As shown in FIG. 3B, a second slide accepting portion 74 which accepts the second slide member 56 to allow its movement in a predetermined range is formed on the outer peripheral surface of the cylindrical portion 62 on the proximal side. An outwardly protruding convex portion 74a is formed on a proximal end portion side of the second slide accepting portion 74. As shown in FIGS. 3A and 3B, the luer mouth ring 64 is arranged between these first and second slide accepting portions 72 and 74.

Figure 4:
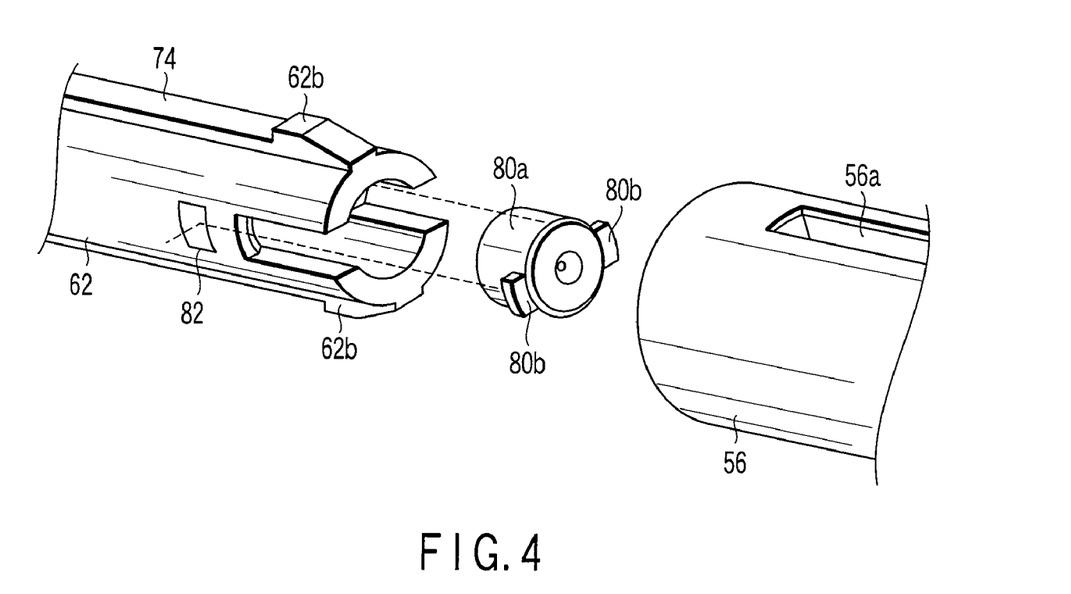
FIG. 4 is a schematic exploded perspective view showing a relationship between an operation portion main body, a second slide member, and a packing material of the operation portion in the endoscopic puncture needle according to the embodiment.

As shown in FIG. 4, a pair of slits 56a (one of the pair is not depicted) are formed in the second slide member 56 in the axial direction. Here, although the second slid member 56 is explained as a representative example, the first slide member 54 has the same structure. A pair of engagement portions 62b are formed on the proximal end side of the second slide accepting portion 74. That is, the pair of outwardly protruding engagement portions 62b are formed on the outer peripheral surfaces of the distal end portion and the proximal end portion of the cylindrical portion 62. The pair of engagement portions 62b on the proximal end side of the second slide accepting portion 74 are engaged with the pair of slits 56a of the second slide member 56. Therefore, the second slide member 56 can be moved with respect to the operation portion main body 52 along the slits 56a.

As shown in FIG. 3A, a click engagement portion 54b which is clicked and engaged with an expanded diameter portion 62c at the proximal end portion of the first slide accepting portion 72 is formed at the proximal end portion of the first slide member 54, i.e., the proximal end portion of slits 54a. As shown in FIG. 3B, a click engagement portion 56b which is clicked and engaged with the distal end portion of the second slide accepting portion 74 is formed at the distal end portion of the second slide member 56, i.e., an expanded diameter portion 62d at the distal end portion of the slits 56a. Therefore, each of the first and second slide members 54 and 56 can move a distance between the click engagement portion 62a or 62b and the expanded diameter portion 62c or 62d.

As shown in FIG. 3A, the outer needle moving member 40 is extended to a position near the inner side of the slits 54a of the first slide member 54. A cylindrical outer needle operation tube 44 is arranged on the inner peripheral surface of the outer needle moving member 40 at the proximal end portion, and it is fixed by press fitting or an adhesive. An outer peripheral surface of the outer needle operation tube 44 is fixed on the inner peripheral surface of the inner space of the cylindrical portion 62 at the distal end portion by an adhesive. Therefore, the outer needle operation tube 44 can slide with respect to the outer needle moving member 40 when the first slide member 54 slides with respect to the operation portion main body 52. It is to be noted that a proximal face of the outer needle moving member 40 comes into contact with an edge of the distal end portion of the cylindrical portion 62 when the click engagement portion 54b of the first slide member 54 is clicked and engaged with the expanded diameter portion 62c. At this time, the outer needle 32 is fixed to the sheath 12.

Figure 5:
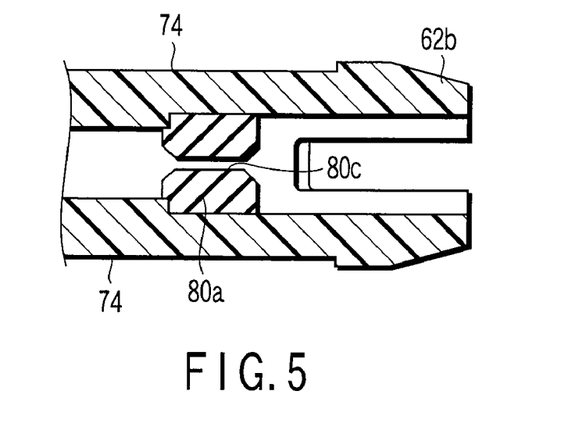
FIG. 5 is a schematic vertical sectional view showing a state in which the packing material is arranged at a proximal end portion of the operation portion main body in the endoscopic puncture needle according to the embodiment.
Figure 6A:
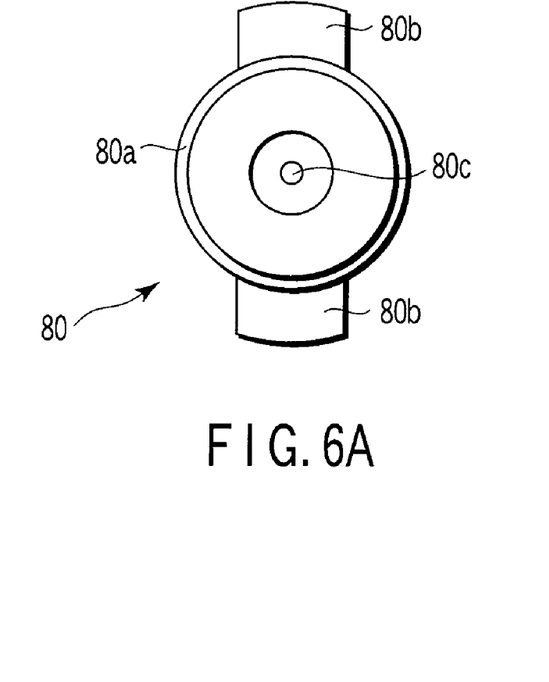
FIG. 6A is a schematic front view showing the packing material arranged at the proximal end portion of the operation portion main body in the endoscopic puncture needle according to the embodiment.
Figure 6B:
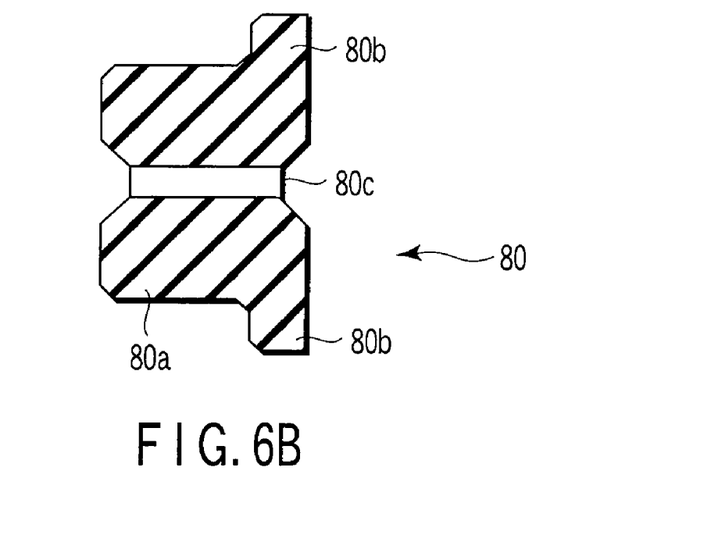
FIG. 6B is a schematic vertical sectional view showing the packing material arranged at the proximal end portion of the operation portion main body in the endoscopic puncture needle according to the embodiment.
Figure 7:
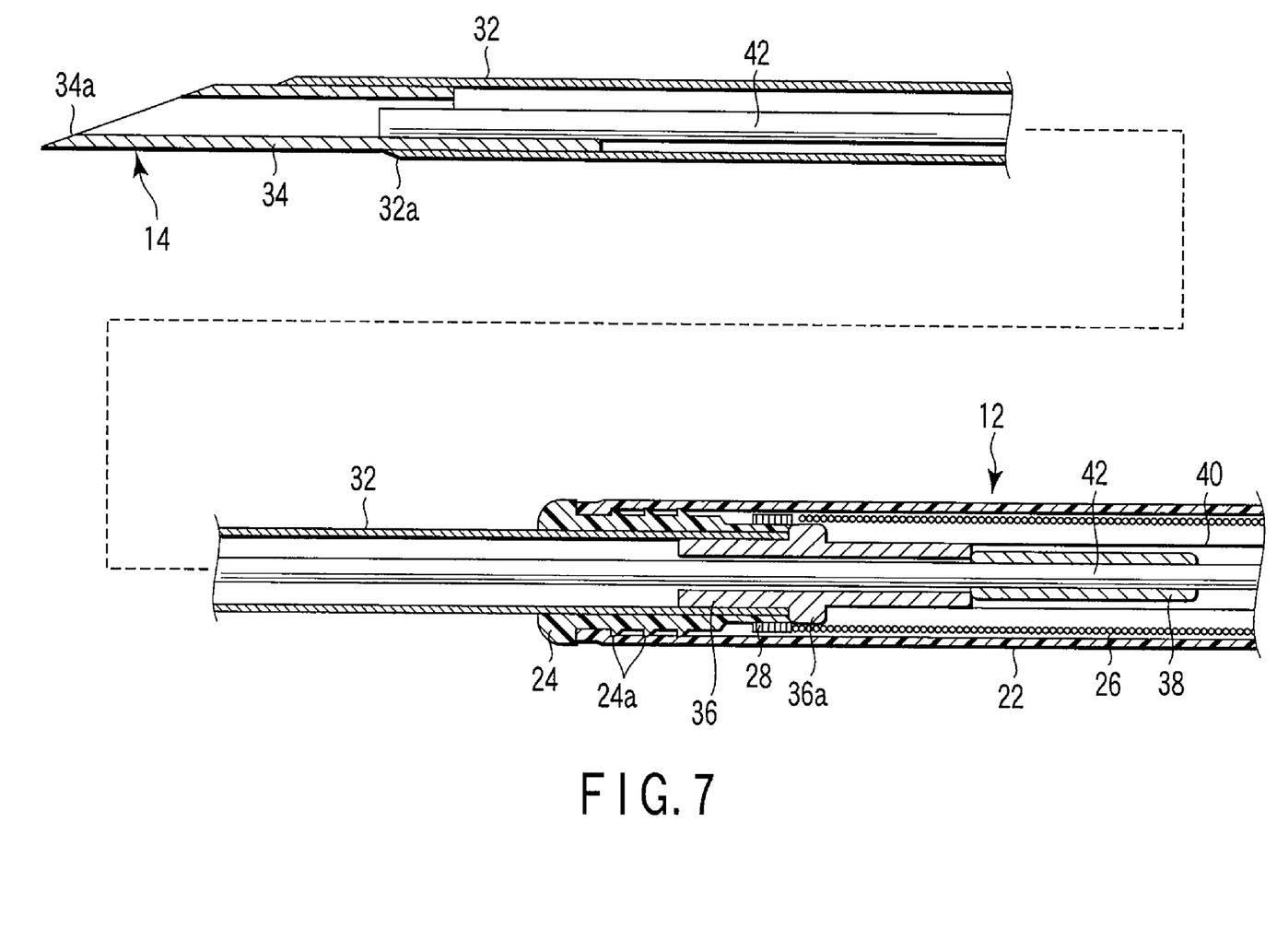
FIG. 7 is a schematic vertical sectional view showing the distal end portion of the endoscopic puncture needle according to the embodiment, especially a state in which a distal end of an inner needle locking member is in contact with a proximal end of an outer needle locking member, the outer needle locking member is in contact with a stopper of the sheath, and a distal end of an inner needle protrudes with respect to a distal end of an outer needle.

The inner needle moving member 42 is fixed to the proximal end portion of the second slide member 56 through the inside of the outer needle moving member 40 and the inside of the outer needle operation tube 44. As shown in FIGS. 4 and 5, a packing material 80 into which the inner needle moving member 42 is inserted is arranged on the inner peripheral surface of the proximal end portion of the cylindrical portion 62. As shown in FIGS. 6A and 6B, the packing material 80 includes a packing main body (a seal member) 80a, and a fitting portion (an engagement mechanism) 80b protruding from the packing main body 80a. As shown in FIG. 4, the fitting portion 80b is fitted in an opening portion 82 formed in the proximal end portion of the cylindrical portion 62. The packing main body 80a is formed of, e.g., an elastic rubber material. At this time, the packing main body 80a is fixed in a state in which it is pushed and pressed against the cylindrical portion 62.

A through hole 80c which is slightly smaller or slightly larger than an outside diameter of the inner needle moving member 42 is formed in the packing main body 80a. Therefore, flows of liquid and gas on the distal end side and the proximal end side of the packing main body 80a are interrupted when the packing material 80 is disposed in the cylindrical portion 62 and the inner needle moving member 42 is arranged in the through hole 80c of the packing main body 80a.

As shown in FIG. 3A, a connecting portion 54c is formed on the outer peripheral surface of the distal end portion of the first slide member 54. A connection tube 58 is detachably arranged on the connecting portion 54c. The connection tube 58 holds the proximal end portion of the sheath 12, i.e., the proximal end portion of the sheath main body 22.

An annular concave portion 54d is formed on the outer peripheral surface of the distal end portion of the connecting portion 54c. An attachment portion 22a connected with the outer peripheral surface of the distal end portion of the connecting portion 54c is formed at the proximal end portion of the sheath main body 22. A sheath concave portion 22b formed along the concave portion 54d is formed in the attachment portion 22a. Therefore, the attachment portion 22a of the sheath main body 22 is formed into the same shape as the outer peripheral surface of the distal end portion of the first slide member 54.

On the other hand, the connection tube 58 includes a distal end engagement portion 58a and a proximal end engagement portion 58b which can be engaged with the distal end portion of the first slide member 54 at the distal end portion and the proximal end portion thereof. The distal end engagement portion 58a is formed to inwardly protrude with respect to the circular tube in the radial direction. The distal end engagement portion 58a can be engaged with the concave portion 54d on the outer peripheral surface of the distal end portion of the first slide member 54 and the sheath concave portion 22b of the attachment portion 22a of the sheath main body 22. The proximal end engagement portion 58b is formed into the same shape as the proximal end portion of the connecting portion 54c of the first slide member 54 and engaged with the proximal end portion.

As shown in FIG. 3B, a bent portion 42a is formed to the inner needle moving member 42 arranged at the proximal end portion of the second slide member 56 in the operation portion 16. The bent portion 42a is engaged with the proximal end portion of the second slide member 56. Therefore, the inner needle moving member 42 can be moved with respect to the sheath 12 or the operation portion 16 when the second slide member 56 is moved with respect to the second slide accepting portion 74.

Incidentally, in regard to the first and second slide members 54 and 56, a moving resistance (a sliding resistance) of the second slide member 56 may be set larger than a moving resistance (a sliding resistance) of the first slide member 54 or vice versa, thereby changing the operability.

A function of the endoscopic puncture needle 10 according to the embodiment will now be explained.

In a first state, the click engagement portion 54b of the first slide member 54 is engaged with the expanded diameter portion 62c of the cylindrical portion 62 in advance, for example. Additionally, the click engagement portion 56b of the second slide member 56 is engaged with the expanded diameter portion 62d of the cylindrical portion 62 in advance, for example.

Here, when the first slide member 54 in the operation portion 16 is moved with respect to the cylindrical portion 62, the sheath main body 22 is moved based on the movement of the first slide member 54. That is, the sheath 12 is moved based on the movement of the first slide member 54. When the second slide member 56 in the operation portion 16 is moved with respect to the cylindrical portion 62, the inner needle moving member 42 is moved based on the movement of the second slide member 56. That is, the inner needle 34 is moved based on the movement of the second slide member 56.

As shown in FIG. 2, the distal end of the needle member 14 in the endoscopic puncture needle 10, i.e., the distal ends of the inner needle 34 and the outer needle 32 are retracted in the distal end of the sheath 12 in order to be inserted into the surgical instrument insertion channel of the endoscope.

In this case, the first slide member 54 of the operation portion 16 is arranged at the most distal end side position of the cylindrical portion 62. On the other hand, the second slide member 56 is arranged at the most proximal end side position of the cylindrical portion 62. That is, the click engagement portion 54b of the first slide member 54 is brought into contact with the click engagement portion 62a beyond the convex portion 72a to engage the first slide member 54 with the distal end of the cylindrical portion 62. On the other hand, the click engagement portion 56b of the second slide member 56 is brought into contact with the click engagement portion 62b beyond the convex portion 74a to engage the second slide member 56 with the proximal end of the cylindrical portion 62.

At this time, the distal end 32a of the outer needle 32 is protruding from the distal end 34a of the inner needle 34. Since the inner needle moving member 42 is retracted to the innermost position with respect to the distal end of the sheath 12, the outer needle moving member 40 is also arranged to be retracted to the innermost position with respect to the distal end of the sheath 12 by the outer needle locking member 36 coming into contact with the proximal end portion of the inner needle 34. At this time, the proximal end of the outer needle locking member 36 comes into contact with the distal end of the inner needle locking member 38. Therefore, the outer needle locking member 36 is pushing the inner needle locking member 38 toward the proximal end side of the sheath 12. Accordingly, the outer needle moving member 40 and the inner needle moving member 42 are bent in the sheath 12 or in the operation portion 16.

A distal end portion of an insertion portion of the non-illustrated endoscope is introduced to a position where it faces a part near a target region of a living body. In this state, the endoscopic puncture needle 10 having the inner needle 34 and the outer needle 32 being pulled in the sheath 12 is inserted from a forceps valve of the surgical instrument insertion channel of the endoscope. Further, the distal end of the sheath 12 is made to protrude from the distal end portion of the insertion portion.

Then, the outer needle 32 and the inner needle 34 are made to protrude from the distal end of the sheath 12 to acquire tissue from the target region.

In this case, the first slide member 54 of the operation portion 16 is arranged at a position close to the luer mouth ring 64 of the cylindrical portion 62. On the other hand, the second slide member 56 is arranged at a position close to the luer mouth ring 64 of the cylindrical portion 62. That is, the click engagement portion 54b of the first slide member 54 is engaged with the expanded diameter portion 62c beyond the convex portion 72a. On the other hand, the click engagement portion 56b of the second slide member 56 is engaged with the expanded diameter portion 62d beyond the convex portion 74a.

At this time, the sheath 12 is moved to the proximal end side of the operation portion 16 based on the movement of the first slide member 54. Furthermore, the inner needle moving member 42 is moved to the distal end side based on the movement of the second slide member 56. The inner needle moving member 42 moves to the distal end side of the sheath 12 to correct flexure of itself. Therefore, the inner needle locking member 38 pushes the outer needle locking member 36 toward the distal end side of the sheath 12, and the inner needle locking member 38 and the outer needle locking member 36 move toward the distal end side of the sheath 12 in an integrated manner. Therefore, flexure of the outer needle moving member 40 is also corrected.

Therefore, the inner needle 34 connected with the distal end of the inner needle moving member 42 moves in a direction such that it protrudes with respect to the distal end of the sheath 12, and the outer needle 32 connected with the proximal end portion of the outer needle locking member 36 also moves in a direction such that it protrudes with respect to the distal end of the sheath 12. At this time, the outer needle locking member 36 is engaged with the inner peripheral surface of the stopper 24 of the sheath 12. Therefore, the outer needle 32 is positioned with respect to the distal end of the sheath 12. The distal end of the inner needle 34 is made to protrude with respect to the distal end of the outer needle 32 with the movement of the inner needle moving member 42. At this time, the distal end of the inner needle locking member 38 moves until it comes into contact with the proximal end of the outer needle locking member 36.

It is to be noted that flexure of the inner needle moving member 42 remains even if the outer needle locking member 36 is in contact with the inner peripheral surface of the stopper 24. Therefore, a state in which the distal end of the inner needle locking member 38 is in contact with the proximal end of the outer needle locking member 36 is maintained (see FIG. 7). Since the inner needle moving member 42 is formed with the rigidity higher than that of the outer needle moving member 40, such a state is maintained.

When the target region is not punctured yet with the distal ends 34a and 32a of the inner needle 34 and the outer needle 32 in this state, the sheath 12 is moved to be further inserted into the channel in order to puncture the target region with the distal ends 34a and 32a of the inner needle 34 and the outer needle 32. Furthermore, tissue of the target region is drawn into the outer needle 32.

In this case, the second slide member 56 in the operation portion 16 is operated. The second slide member 56 is operated to the farthermost position from the luer mouth ring 64 to which the second slide member 56 can be moved. That is, engagement of the expanded diameter portion 62d with respect to the click engagement portion 56b of the second slide member 56 is released. Moreover, the click engagement portion 56b is moved to the proximal end side along the second slide accepting portion 74. At this time, the click engagement portion 56b is moved until it comes into contact with the engagement portion 62b beyond the convex portion 74a of the second slide accepting portion 74. Therefore, the inner needle moving member 42, the inner needle locking member 38, and the inner needle 34 are pulled into the outer needle operation tube 44, the outer needle moving member 40, the outer needle locking member 36, and the outer needle 32. Then, the distal end 34a of the inner needle 34 is retracted with respect to the distal end of the outer needle 32. Therefore, the distal end of the inner needle locking member 38 moves away from the proximal end of the outer needle locking member 36 (see FIG. 2).

In this state, a syringe (not shown) is attached to the luer mouth ring 64 of the operation portion 16. The syringe sucks the inside of the cylindrical portion 62 of the operation portion main body 52. A suction force at this time is transmitted to the inner space of the outer needle 32 through the outer needle operation tube 44, the outer needle moving member 40, and the outer needle locking member 36, thus reducing pressures in these members. Therefore, the tissue of the target region is drawn into the inner space of the outer needle 32. At this time, although the inner needle 34 is arranged in the inner space of the outer needle 32 in a retracted state, the tissue is prevented from entering at the time of puncturing the target region, and hence the inner space of the outer needle 32 is assured. Therefore, a larger amount of the tissue which is an allowed amount obtained by the inner space of the outer needle 32 or close to it can be acquired.

After suction, the syringe is removed from the luer mouth ring 64 of the operation portion 16. Then, engagement achieved between the click engagement portion 54b of the first slide member 54 and the expanded diameter portion 62c of the first slide accepting portion 72 in the operation portion 16 is released. Additionally, the first slide member 54 is operated to a movable position where it is kept on the luer mouth ring 64 so that the outer needle 32 is retracted with respect to the distal end of the sheath 12. That is, the distal end of the outer needle 32 is pulled out from the target region. Further, the click engagement portion 54b of the first slide member 54 is brought into contact with the click engagement portion 62a beyond the convex portion 72a so that the first slide member 54 is locked at the distal end of the cylindrical portion 62. Therefore, the distal end 32a of the outer needle 32 is pulled into the distal end of the sheath 12.

Furthermore, the endoscopic puncture needle 10 is pulled out from the surgical instrument insertion channel of the endoscope.

Thereafter, the luer mouth ring 64 supplies, e.g., pressurized air to extract (collect) a biomedical tissue collected in the inner space of the outer needle 32 from the distal end of the outer needle 32. The biomedical tissue extracted in this manner is subjected to various kinds of examinations.

It is to be noted that, when acquiring the tissue, the order of moving the first and second slide members 54 and 56 is not restricted to the above-explained order, and they may be moved in the opposite order.

As explained above, according to this embodiment, the following effect can be obtained.

Since the needle member 14 is formed into a double structure in which the inner needle 34 can protrude from the outer needle 32, retracting the inner needle 34 alone after a target region is punctured with the needle member 14 enables providing a space in the outer needle 32. Therefore, a larger amount of a desired tissue can be drawn into the inner space of the outer needle 32.

Moreover, since the rigidity of the inner needle moving member 42 is higher than that of the outer needle moving member 40, the flexibility which enables insertion into the surgical instrument insertion channel of the endoscope can be assured while assuring a tensile force when puncturing a target region with both the inner needle 34 and the outer needle 32.

Additionally, the packing material 80 which is used to maintain a suction force in the outer needle 32 is fixed and hermetically contained by just being pushed into the second slide accepting portion 74 of the cylindrical portion 62, facilitating assembling the operation portion 16.

Although the embodiment has been specifically explained above with reference to the drawings, the present invention is not restricted to the foregoing embodiment, and all embodiments carried out without departing from the scope of the invention are included.

What is claimed is:

1. An endoscopic puncture needle comprising:
a sheath having flexibility;
a hollow outer needle which is movable along an axial direction of the sheath in the sheath and whose distal end is retractable with respect to a distal end of the sheath;
an inner needle which moves along the axial direction of the sheath in the outer needle and is retractable with respect to the distal end of the outer needle;
an outer needle moving mechanism for moving the outer needle with respect to the sheath;
an inner needle moving mechanism for moving the inner needle with respect to the outer needle;
an operation portion which is arranged at a proximal end portion of the sheath and operates the outer needle moving mechanism and the inner needle moving mechanism;
a duct which runs through an inner space of the outer needle and an inner space of the outer needle moving mechanism and communicates with the operation portion; and
a packing material which air-tightly holds the duct at all times;
wherein the packing material includes:
a seal member having a through hole through which the inner needle moving mechanism is inserted; and
an engagement mechanism which is positioned on the seal member and is engaged with the operation portion.

2. The endoscopic puncture needle according to claim 1, wherein the outer needle moving mechanism is set to a length which produces flexure in the sheath when the outer needle is made to protrude to a maximum extent from the distal end of the sheath.

3. The endoscopic puncture needle according to claim 1, wherein
the operation portion includes an operation portion main body having a cylindrical portion;
the engagement mechanism includes a fitting portion projecting from the seal member; and
the cylindrical portion has an opening, in which the fitting portion of the packing material is fitted, at a proximal end portion of the cylindrical portion.

4. The endoscopic puncture needle according to claim 1, wherein
the operation portion includes an operation portion main body having a cylindrical portion; and
the seal member is formed of a columnar elastic material and pushed against the cylindrical portion of the operation portion main body.

5. The endoscopic puncture needle according to claim 1, wherein
the operation portion includes a mouth ring communicating with an inside of the operation portion and the inner space of the outer needle, the mouth ring being attached to a syringe;
the packing material is positioned between the mouth ring and a proximal end portion of the operation portion; and
the endoscopic puncture needle is configured to draw tissue of a target region into at least one of the outer needle and the inner needle even in a state where the inner needle is retracted into the inner space of the outer needle by suction force of the syringe.

6. The endoscopic puncture needle according to claim 5, wherein
the operation portion includes a first slide member which moves the sheath in its axial direction, and a second slide member which moves the inner needle moving mechanism and the inner needle in its axial direction; and
the mouth ring is positioned between the first slide member and the second slide member.

7. An endoscopic puncture needle, comprising:
a sheath having flexibility;

a hollow outer needle which is movable along an axial direction of the sheath in the sheath and whose a distal end is retractable with respect to a distal end of the sheath;

an outer needle moving mechanism disposed at a proximal end of the outer needle and moving the outer needle with respect to the sheath;

an inner needle which moves along the axial direction of the sheath in the outer needle and is retractable with respect to the distal end of the outer needle;

an inner needle moving mechanism disposed at a proximal end of the inner needle and moving the inner needle with respect to the outer needle;

an operation portion disposed at a proximal end portion of the sheath and operating the outer needle moving mechanism and the inner needle moving mechanism;

a duct which runs through an inner space of the outer needle and an inner space of the outer needle moving mechanism and communicates with the operation portion; and a packing material which is positioned in the operation portion and which air-tightly holds the duct at all times;

wherein the packing material includes:
    a seal member having a through hole through which the inner needle moving mechanism is inserted; and
    an engagement mechanism which is positioned on the seal member and is engaged with the operation portion.

8. The endoscopic puncture needle according to claim 7, wherein
    the operation portion includes an operation portion main body having a cylindrical portion;
    the engagement mechanism includes a fitting portion projecting from the seal member; and
    the cylindrical portion has an opening, in which the fitting portion of the packing material is fitted, at a proximal end portion of the cylindrical portion.

9. The endoscopic puncture needle according to claim 7, wherein
    the operation portion includes an operation portion main body having a cylindrical portion; and
    the seal member is formed of a columnar elastic material and pushed against the cylindrical portion of the operation portion main body.

10. The endoscopic puncture needle according to claim 7, wherein
    the operation portion includes a mouth ring communicating with an inside of the operation portion and the inner space of the outer needle, the mouth ring being attached to a syringe;
    the packing material is positioned between the mouth ring and a proximal end portion of the operation portion; and
    the endoscopic puncture needle is configured to draw tissue of a target region into at least one of the outer needle and the inner needle even in a state where the inner needle is retracted into the inner space of the outer needle by suction force of the syringe.

11. The endoscopic puncture needle according to claim 10, wherein
    the operation portion includes a first slide member which moves the sheath in its axial direction, and a second slide member which moves the inner needle moving mechanism and the inner needle in its axial direction; and
    the mouth ring is positioned between the first slide member and the second slide member.

* * * * *